US008795504B2

(12) United States Patent
Petrossians et al.

(10) Patent No.: US 8,795,504 B2
(45) Date of Patent: Aug. 5, 2014

(54) ELECTRODEPOSITION OF PLATINUM/IRIDIUM (PT/IR) ON PT MICROELECTRODES WITH IMPROVED CHARGE INJECTION PROPERTIES

(75) Inventors: Artin Petrossians, Glendale, CA (US); Artak Arakelian, Los Angeles, CA (US); James D. Weiland, Valencia, CA (US); Florian B. Mansfeld, Los Angeles, CA (US); John J. Whalen, III, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 240 days.

(21) Appl. No.: 12/870,702

(22) Filed: Aug. 27, 2010

(65) Prior Publication Data
US 2011/0048955 A1 Mar. 3, 2011

Related U.S. Application Data

(60) Provisional application No. 61/237,619, filed on Aug. 27, 2009.

(51) Int. Cl.
*C25D 3/56* (2006.01)

(52) U.S. Cl.
USPC ............................ 205/257; 205/255; 205/259

(58) Field of Classification Search
USPC ......................................... 205/255, 257, 259
See application file for complete search history.

(56) References Cited

U.S. PATENT DOCUMENTS 6,207,036 B1 * 3/2001 de Vries ........................ 205/237
6,974,533 B2 12/2005 Zhou
2002/0034676 A1 * 3/2002 Kim et al. ........................ 429/44
2002/0144909 A1 * 10/2002 Ueki .............................. 205/265
2008/0268138 A1 * 10/2008 Reddington et al. ......... 427/96.1

OTHER PUBLICATIONS

Ureta-Zanartu et al., "Electrodeposited Pt-Ir Electrodes: Characterization and Electrocatalytic Activity for the Reduction of the Nitrate Ion", J. Solid State Electrochem (no month, 1998), vol. 2, pp. 191-197.*
Cogan, S.F. et al. 2004. Sputtered Iridium Oxide Films (SIROFs) for Neural Stimulation Electrodes. Conference Proceedings IEEE Eng. Med. Biol. Soc. 2004, vol. 6, pp. 4153-4156.
Cui, X.T. et al. 2007. Poly (3,4-Ethylenedioxythiophene) for Chronic Neural Stimulation. IEEE Transactions on Neural Systems and Rehabilitation Engineering, Dec. 2007, vol. 15, No. 4, pp. 502-508.

(Continued)

*Primary Examiner* — Edna Wong
(74) *Attorney, Agent, or Firm* — McDermott Will & Emery LLP

(57) ABSTRACT

Aspects of the present disclosure are directed to electrochemical approaches for synthesis of platinum-iridium alloys with selected platinum-iridium ratio content and subsequently predetermined mechanical properties and electrochemical impedance properties. Such can provide a simple and cost-effective process for preparing these electrodes, as compared to conventional thin film processing techniques. A three-electrode electrochemical electrodeposition system is described including an electrochemical cell with a working electrode on which the electrodeposited film is deposited, a counter electrode to complete the electrochemical circuit and a reference electrode to measure and control surface potential. Mixed layers of platinum atoms and iridium atoms can be deposited from electrolyte solution onto the working electrode surface to create an electrically conductive surface with material properties related to the composition of the as-deposited film. The mechanical properties and electrochemical properties of the film can be tuned by adjusting the electrodeposition parameters.

22 Claims, 12 Drawing Sheets

(56) References Cited

OTHER PUBLICATIONS

Meyer, R.D. et al. 2001. Electrodeposited Iridium Oxide for Neural Stimulation and Recording Electrodes. IEEE Transactions on Neural Systems and Rehabilitation Engineering, Mar. 2001, vol. 9, No. 1, pp. 2-11.

Slavcheva, E. et al. 2004. Sputtered Iridium Oxide Films as Charge Injection Material for Function Electrostimulation. Journal of the Electrochemical Society, vol. 151, No. 7, pp. E226-E237.

Tykocinski, M. et al. 2001. Chronic Electrical Stimulation of the Auditory Nerve Using High Surface Area (HiQ) Platinum Electrodes. Hearing Research, vol. 159, pp. 53-68.

Wang, K. et al. 2006. Neural Stimulation with a Carbon Nanotube Microelectrode Array. Nano Letters, vol. 6, No. 9, pp. 2043-2048.

Whalen, J.J. III et al. 2005. Electrochemical Deposition of Platinum from Aqueous Ammonium Hexachloroplatinate Solution. Journal of the Electrochemical Society, vol. 152, No. 11, pp. C738-C743.

* cited by examiner

US 8,795,504 B2

ELECTRODEPOSITION OF PLATINUM/IRIDIUM (PT/IR) ON PT MICROELECTRODES WITH IMPROVED CHARGE INJECTION PROPERTIES

STATEMENT REGARDING FEDERALLY SPONSORED RESEARCH

This invention was made with government support under Contract No. EEC0310723 awarded by the National Science Foundation. The government has certain rights in the invention.

RELATED APPLICATION

This application claims the benefit of U.S. Provisional Patent Application No. 61/237,619, filed 27 Aug. 2009 and entitled "Electrodeposition of Platinum/Iridium (Pt/Ir) on Pt Microelectrodes with Improved Charge Injection Properties," the entire content of which is incorporated herein by reference.

BACKGROUND

Small-scale microelectrodes are used in a number of applications. One promising field of application of microelectrodes is for neural prosthetic medical devices, which are typically used to stimulate nerve cells to overcome pre-existing medical conditions. Examples of such medical conditions include diseases producing damage to the retina such as uveitis, retinitis pigmentosa, macular degeneration, diabetic retinopathy and glaucoma. Metallic microelectrodes have been used for neural prosthetic medical devices. Platinum and platinum-based alloys have proven useful for such microelectrodes because of the high degree of bio-compatibility afforded.

Platinum and iridium, and the platinum group metals in general, possess the unique qualities of having multiple oxidation states, conducting oxides, low electrochemical impedance, and enhanced biocompatibility in electrical stimulating and sensing applications over other conducting metal materials. These qualities position both platinum and iridium as prime choices for electrode composition in applications such as fuel cell electrodes, hydrolysis reactions electrodes, and implantable electrodes for sensing and stimulating. Individually, platinum and iridium possess different mechanical properties. Platinum is known to be ductile and malleable, while iridium is known to be stiff and brittle. The two are often alloyed to create alloys with improved mechanical properties over the individual constituents. The exact ratio of the two is adjusted so as to match the mechanical property requirements for the particular application, e.g. more platinum where a more ductile electrode is preferred and more iridium were stiffness is desired. A common quality of both materials is high melting temperature, platinum (1772° C.) and iridium (2410° C.). This makes processing and handling of both metals a challenge, particularly in the manufacturing of small components. A variety of thin film processing techniques have been used to create components and features of this size, e.g., electron beam evaporation and magnetron sputtering in concert with photolithography and other semi-conductor processing techniques; however, these processes are performed under high-vacuum which is not time-efficient or cost-effective. Additionally, these are thin film coating processes that coat series of mono-atomic layers of metal throughout the deposition chamber thus being source-material inefficient.

Another quality of both metals worth noting is their low electrochemical impedance. This is attributable to the multiple oxidation states of both elements, as well as, the electrical conductivity of their oxides that allow for easier electron transfer between the metal and a surrounding electrolyte solution. Iridium possesses more oxidation states and its oxide possesses a lower electrical resistance therefore it shows lower electrochemical impedance over platinum and platinum oxide.

Some previous techniques for electroplating platinum and/or platinum iridium have been reported. Such techniques, however, have typically utilized corrosive and/or toxic solutions. Moreover, such techniques have produced microelectrodes having less than ideal mechanical properties and/or electrical properties.

SUMMARY

Aspects of the present disclosure can provide for efficient technique for electrodepositing platinum-iridium (Pt—Ir) alloy electrodes. Pt—Ir alloy microelectrodes according to the present disclosure can demonstrate improved mechanical properties, e.g., plating adhesion, modulus of elasticity, shear modulus, fatigue strength, etc., and enhanced charge injection properties over standard platinum electrodes.

An aspect of the present disclosure is directed to a method of depositing a platinum-iridium alloy or desired mixture of platinum and iridium atoms/molecules onto a base, e.g., a gold of platinum foil or wire. The method can include causing contact (e.g., immersion) between a metal base and an electrolyte solution for electrodeposition, with the electrolyte solution being biosafe or non-cytotoxic and including platinum and iridium. Two or more electrodes can be caused to come into contact with or presented to or placed in the electrolyte solution. The electrodes can be configured to apply an electric potential to or through the electrolyte solution. At least one of the two or more electrodes can be caused to come into electrical contact with the metal base. An electric potential can be applied to or across the electrodes in the electrolyte solution in an amount or to a degree sufficient cause deposition of Pt—Ir on the metal base. The deposition can be controlled to produce a desired composition ratio of Pt to Ir.

A further aspect of the present disclosure is directed to a Pt/Ir microelectrode. The microelectrode can include a metal base of a selected metal composition, and a Pt/Ir film disposed on the metal base. The Pt/Ir film has a desired composition ratio of Pt to Ir. In exemplary embodiments, the microelectrode can be cylindrical with a desired length and a diameter of between about 0.5 micron to about 200 micron (or any diameter within the range, inclusive of the end values). Other diameters of such microelectrodes (which may be any practical shape) may of course be realized within the scope of the present disclosure.

These, as well as other components, steps, features, benefits, and advantages of the present disclosure, will now become clear from a review of the following detailed description of illustrative embodiments, the accompanying drawings, and the claims.

BRIEF DESCRIPTION OF DRAWINGS

The drawings disclose illustrative embodiments. They do not set forth all embodiments. Other embodiments may be used in addition or instead. Details that may be apparent or unnecessary may be omitted to save space or for more effective illustration. Conversely, some embodiments may be practiced without all of the details that are disclosed. When the same numeral appears in different drawings, it refers to the same or like components or steps.

Aspects of the disclosure may be more fully understood from the following description when read together with the accompanying drawings, which are to be regarded as illustrative in nature, and not as limiting. The drawings are not necessarily to scale, emphasis instead being placed on the principles of the disclosure. In the drawings.

Figure 1:
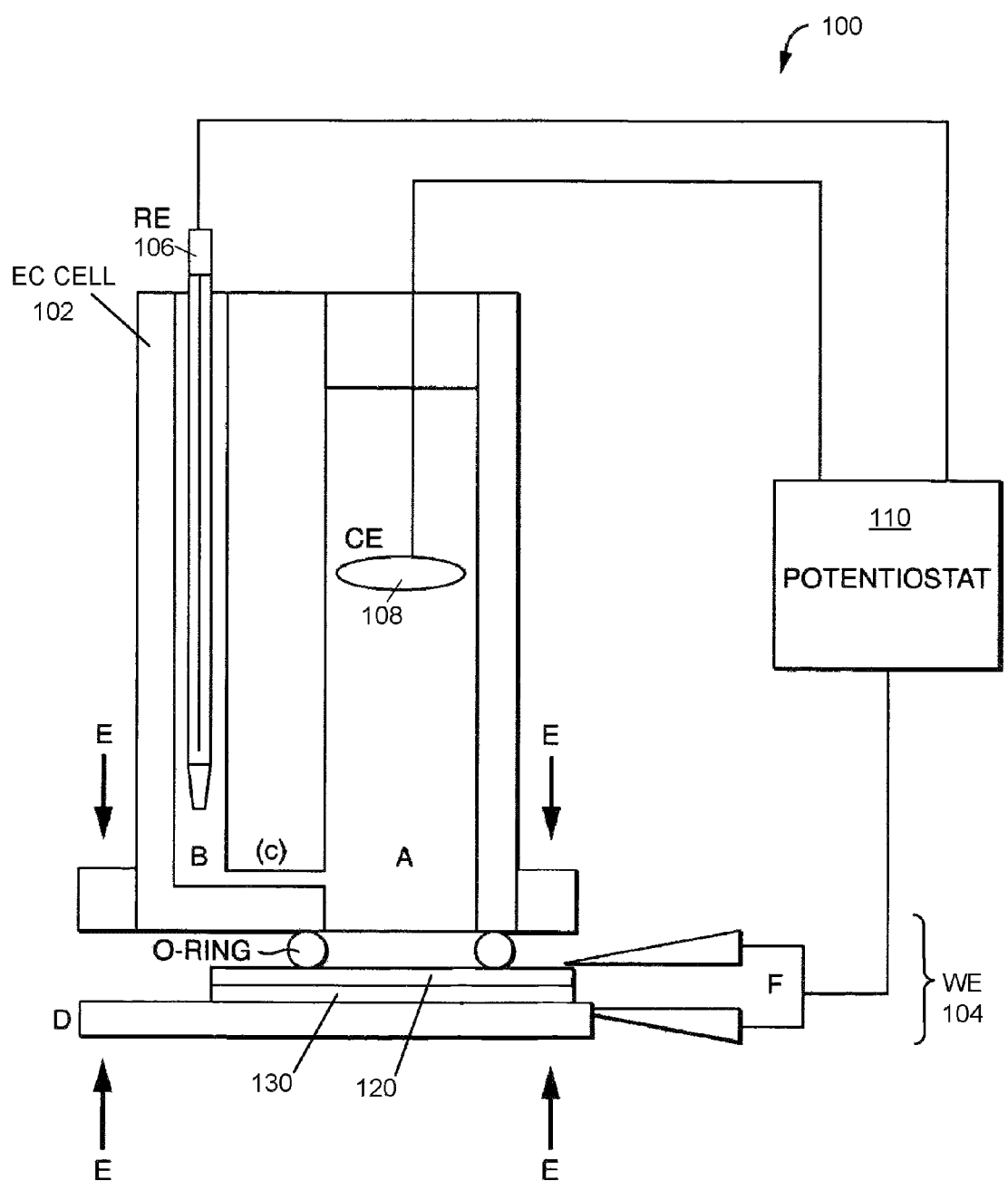
FIG. 1 depicts a three-electrode electrochemical cell made of Teflon, as used for exemplary embodiments of the present disclosure.

While certain embodiments are depicted in the drawings, one skilled in the art will appreciate that the embodiments depicted are illustrative and that variations of those shown, as well as other embodiments described herein, may be envisioned and practiced within the scope of the present disclosure.

DETAILED DESCRIPTION OF ILLUSTRATIVE EMBODIMENTS

Illustrative embodiments are now discussed. Other embodiments may be used in addition or instead. Details that may be apparent or unnecessary may be omitted to save space or for a more effective presentation. Conversely, some embodiments may be practiced without all of the details that are disclosed.

Aspects of the present disclosure provide for Pt—Ir electrodes or desired composition and also related fabrication methods with electrodeposition utilizing novel plating electrolyte solutions and/or using unique deposition methods.

The deposition processes can be controlled in such a way as to produce Pt—Ir thin films with desired composition and microstructure. For example, embodiments of the present disclosure can provide programs for producing thin films of 90% Pt-10% Ir, 95%-5% Pt—Ir, 60%-40% Pt—Ir, etc. Thus, control techniques are provided for deposition conditions to control Pt—Ir conditions to predictably produce a thin film electrode with predetermined composition and properties.

Potentiodynamic deposition (deposition using non-steady-state control of the potential) can be used for exemplary embodiments of the present disclosure. For example, a varying, non-steady-state potential, e.g., subject to cycling, cyclic potential stepping, and/or triangular-wave (ramp) cycling (within a maximum and minimum potential limit), can also be used to deposit metal. These cyclic or non-steady-state approaches deposit metal for a fixed portion of the cycle, then change the potential to allow byproducts of the deposition reaction to leave the active, deposition surface and provide time for new metal reactant to migrate to the deposition surface or to allow preferential deposition of one of the two species.

Generally, deposition can, and preferably does, employ a potential cycling, e.g., a sweeping, stepping, and/or pulsing process, which drives the surface potential of the working electrode over a potential range that is negative to the equilibrium potential for reduction of both the Pt cation salt and the Ir cation salt for at least a portion of the potential range. The positive limit of the potential range may be more positive than both or only one limit, e.g., as described below for FIG. 11. Additionally, the rate at which the potential is swept may be adjusted (either using slow or fast rate) to produce thin films with less internal stress. The deposition may be performed under inert gas or non-oxidizing gas ($N_2$) in order to avoid cation oxidation prior to deposition. In some solution chemistries is may be possible to use a potentiostatic deposition program, where the applied potential is more negative than the equilibrium potential of both the Pt and the Ir salts.

Electrodeposition according to the present disclosure can allow for a more time and cost efficient approach to metal deposition over standard metal processing techniques, e.g., casting, forging, sputtering, evaporation, etc.

Aspects and embodiments of the present disclosure broadly relate to the creation of electrodeposited thin films containing platinum and iridium having low-impedance, and more particularly describes a method for creating such thin films through a process that allows control of: (1) platinum and iridium content; (2) mechanical properties; and, (3) electrochemical impedance properties. More specifically, the invention describes the composition of electrolyte solution and electrodeposition variables that can be employed so as to predictably produce thin film electrodes of known and desirable composition, mechanical properties and electrochemical properties. As mentioned above, a Pt—Ir plating solution can be prepared for the deposition of Pt—Ir films of a desired composition ratio. Exemplary embodiments of the present disclosure can use plating solutions according to the following methods to achieve biocompatibility; other Pt—Ir solutions can of course be used within the scope of the present disclosure.

In exemplary biocompatible embodiments of the present disclosure, Pt/Ir films can be electrodeposited from Pt—Ir solution using 0.2 g/L of Sodium hexachloroiridate (III) hydrate, ($Na_3IrCl_6.xH_2O$) and 0.186 g/L Sodium hexachloroplatinate (IV) hexahydrate ($Na_2PtCl_6.6H_2O$) in 0.1 M nitric acid ($HNO_3$). Exemplary embodiments of such solutions were tested, as described below. A plating solution can be boiled and then cooled to room temperature. Before electrodeposition, the Pt—Ir solutions can be pre-heated, e.g., to 62 C. The solutions can be agitated using an ultrasonic homogenizer, e.g., a homogenizer (Misonix, Inc.) at a frequency of 20 kHz with a power of 5 W to maintain constant mass transfer during electrodeposition. The solution(s) can be kept at a constant temperature constant for such. Preparation of solutions may be performed under inert gas or non-oxidizing gas ($N_2$) in order to avoid cation oxidation prior to deposition.

Aspects of the present disclosure are directed to electrochemical approaches for synthesis of platinum-iridium alloys with pre-determined, or selected, platinum-iridium ratio content and subsequently predetermined mechanical properties and electrochemical impedance properties. Such can provide a simple and cost-effective process for preparing these electrodes, as compared to conventional thin film processing techniques.

In a three-electrode electrochemical system comprising an electrochemical cell with a working electrode on which the electrodeposited film is deposited, a counter electrode to complete the electrochemical circuit and a reference electrode to measure and control surface potential, mixed layers of platinum atoms, iridium atoms, and oxides and chlorides of both, are deposited from electrolyte solution onto the working electrode surface to create an electrically conductive surface with material properties related to the composition of the as-deposited film. The mechanical properties and electrochemical properties of the film can be tuned by adjusting the electrodeposition parameters so as to control the composition and structure of the film.

In applications where a low-impedance electrochemical electrode is required for passage of current in the positive or negative direction across the interface, this method would allow for the electrode impedance and mechanical properties to be tailored to meet the design requirements. Impedance can be controlled by controlling the deposited film's surface area and/or platinum-iridium composition ratio. Similarly, where mechanical properties are important, the electrodeposited film can be deposited with more platinum content in applications where more ductile properties are desirable, and with more iridium content when more stiffness and rigidity are required.

FIG. 1 depicts a three-electrode electrochemical system 100 including an electrochemical cell 102 useful for electrodeposition, in accordance with exemplary embodiments of the present disclosure. System 100 can include a working electrode (WE) 104, reference electrode (RE) 106, and counter electrode (CE) 108. System 100 can be connected to a potentiostat 110, e.g., a computer controlled potentiostat. The electrochemical cell 102 can include a larger diameter electrolyte column (A) and a smaller diameter electrolyte column (B), each connected to one another, e.g., at the cell base via a cross-drilled Luggin capillary (C). A Luggin capillary can facilitate creation of a well-defined short electrolytic path between the working electrode (WE) 104 and the reference electrode (RE) 106. The working electrode (WE) 104 can include (or be used with) a conductive layer or plate for electrical connection to electrolytic solution in cell 102, e.g., a conductive plate 120, as shown. A gasket or sealing structure, e.g., a polymer o-ring, can be placed between cell 102 and conductive plate 120 to facilitate a fluid-tight seal, as shown. Conductive plate 120 can be on or adjacent to a substrate 130, which is preferably non-conducting (electrically). Substrate 130 can be placed onto a suitable base or support surface, e.g., a copper plate (D).

Continuing with the description of FIG. 1, in use for deposition, column (A) can be filled with a plating solution, as described in further detail below. An exemplary plating solution can include a Pt—Ir solution using (equal to or about) 0.2 g/L of Sodium hexachloroiridate (III) hydrate, ($Na_3IrCl_6 \cdot xH_2O$) and (equal to or about) 0.186 g/L Sodium hexachloroplatinate (IV) hexahydrate ($Na_2PtCl_6 \cdot 6H_2O$) in 0.1 M nitric acid ($HNO_3$). An electrical connection can be implemented, e.g., including toothless copper alligator clip (F), to make electrical contact between the working electrode lead (WE) and the conductive material layer 120. The counter electrode (CE) 108, e.g., made of platinum mesh, can be suspended through the top opening of the larger column (A). A reference electrode (RE) 106, e.g., made of Ag/AgCl, can be placed in the smaller-barreled column (B) of the cell 102. The cross-drilled Luggin capillary (C) can allow for accurate potential measurement without disrupting the field between the working and counter electrodes 104, 108.

For an exemplary tested embodiment, the cell 102 was made of Teflon. The larger chamber (A) contained the Pt counter electrode and the deposition solution and the smaller chamber contained the reference electrode. The two chambers were connected to each other through a small horizontal small via. Gold coated glass slide substrates were the working electrodes and were placed on a copper plate with the metalized surface facing up and a polymer O-ring was placed on top of the substrate underneath the larger chamber. The area of working electrode was 0.7 $cm^2$. The electrodeposition cell was then fixed over the o-ring using a steel spring clamp.

For exemplary tested embodiments, described in further detail below, surface morphology was characterized via scanning electron microscope (SEM) and the chemical compositions of these films were determined using wavelength dispersive spectroscopy (WDS). The properties of these films were evaluated using CV and electrochemical impedance spectroscopy (EIS) and compared against pure Pt, pure Ir and 80-20% Pt—Ir foils. 60-40% Pt—Ir thin film alloys were deposited with thicknesses ranging from 80 nm to 500 nm varying as a function of electrodeposition time. with a deposition rate of 16.5 nm/min. Characterizations by SEM and EIS revealed that the surface area of Pt—Ir films increased with increasing films thicknesses. The Pt—Ir films were electroplated and evaluated on gold substrate being developed for neural recording and stimulation applications.

For exemplary tested embodiments, thin films were electrodeposited on 1"×3"×0.040" (25 mm×75 mm×1 mm) glass slide substrates coated with a 50 Å chromium adhesion layer covered by a 1000 Å gold layer (EMF Corp). The substrates were chemically cleaned using trichloroethylene, acetone, methanol and finally rinsed with DI water to remove organic impurities. 25×25 mm Pt (99.9%), Ir (99.9%) and 80-20% Pt—Ir (99.9%) foils were mechanically polished and electrochemically cleaned by potential stepping at U=+1.0 V vs. Ag/AgCl and U=−1.0V vs. Ag/AgCl with a duration time of 30 seconds for each potential, repeated 5 cycles before electrochemical measurements. Pt/Ir films were electrodeposited from freshly prepared Pt—Ir solution using 0.2 g/L of Sodium hexachloroiridate (III) hydrate, ($Na_3IrCl_6 \cdot xH_2O$) and 0.186 g/L Sodium hexachloroplatinate (IV) hexahydrate ($Na_2PtCl_6 \cdot 6H_2O$) in 0.1 M nitric acid ($HNO_3$). The plating solution was boiled and then cooled to room temperature. Before electrodeposition, the Pt—Ir solutions were pre-heated to 62 C. The solutions were agitated using an ultrasonic homogenizer (available from Misonix, Inc.) at a frequency of 20 kHz with a power of 5 W to maintain constant mass transfer during electrodeposition and kept the temperature constant. Electrodeposition was performed in a custom electrochemical cell, FIG. 1, using a three-electrode setup. A Gamry potentiostat was used to control potential. Deposition regimens were performed by cycling potential over the range from U=0.1V to −0.1V vs. Ag/AgCl, at a scan rate of 0.5 V/s for 300, 600, 1200 or 2400 cycles (equivalent to 4, 8, 16 and 32 minutes of deposition, respectively). The potential was scanned A series of potentiodynamic cycles experiments was performed and the deposits obtained at different deposition potentials were analyzed by SEM/EDS, allowing us to determine the threshold electrodepositing potential limits corresponding to the maximum amount of Ir to be within +0.1 V to −0.1 V.

Au substrates were weighed before and after each deposition to calculate thin film mass. Film thicknesses were measured twice each by profilometer (Ambios XP-2 Stylus) and averaged to determine average film thickness. Total working distance for each scan was 11 mm. 1 mm sections through the central portion of the film was used from each scan to estimate film thickness.

Pt—Ir thin film surface morphologies were imaged by field emission scanning electron microscope (ZEISS 1550 VP) with accelerating voltage of 4 kV and a magnification of 100. The chemical compositions of the control foils and electrodeposited Pt—Ir films were characterized by Microprobe analysis (JXA-8200). Three different spots were analyzed on all samples.

The electrodeposited Pt—Ir thin films, the control foils and Au substrate, were electrochemically characterized by cyclic voltammetry (CV) in 0.05 M $H_2SO_4$ at a scan rate of 50 mV/s over the potential range U=−0.3V to 1.2V vs Ag/AgCl. Control samples were mechanically polished and rinsed with ethanol and DI water to deoxidize and degrease the samples surfaces prior to characterization. Electrodeposited films were chemically cleaned by ethanol and DI water and then electrochemically cleaned by applying a step potential at U=+1.32 V and U=−0.32 V vs. Ag/AgCl for 30 seconds each, for 2 cycles in 0.05 M $H_2SO_4$ Electrochemical impedance spectroscopy (EIS) was performed on the Pt—Ir films, the control samples and Au substrates. Potentiostatic measurements were performed at the open circuit potential (OCP) with a +/−10 mV amplitude ac signal superimposed in 0.05 M $H_2SO_4$(aq) over the frequency range 100 KHz to 10 MHz using a Gamry FAS1 potentiostat (Gamry Instruments). Experimental data were fitted to a one-time constant equivalent circuit (EC) and the values of the solution resistance ($R_s$), polarization resistance ($R_p$) and capacitance (C) were determined using the ANALEIS software COATFIT module.

Figure 2:
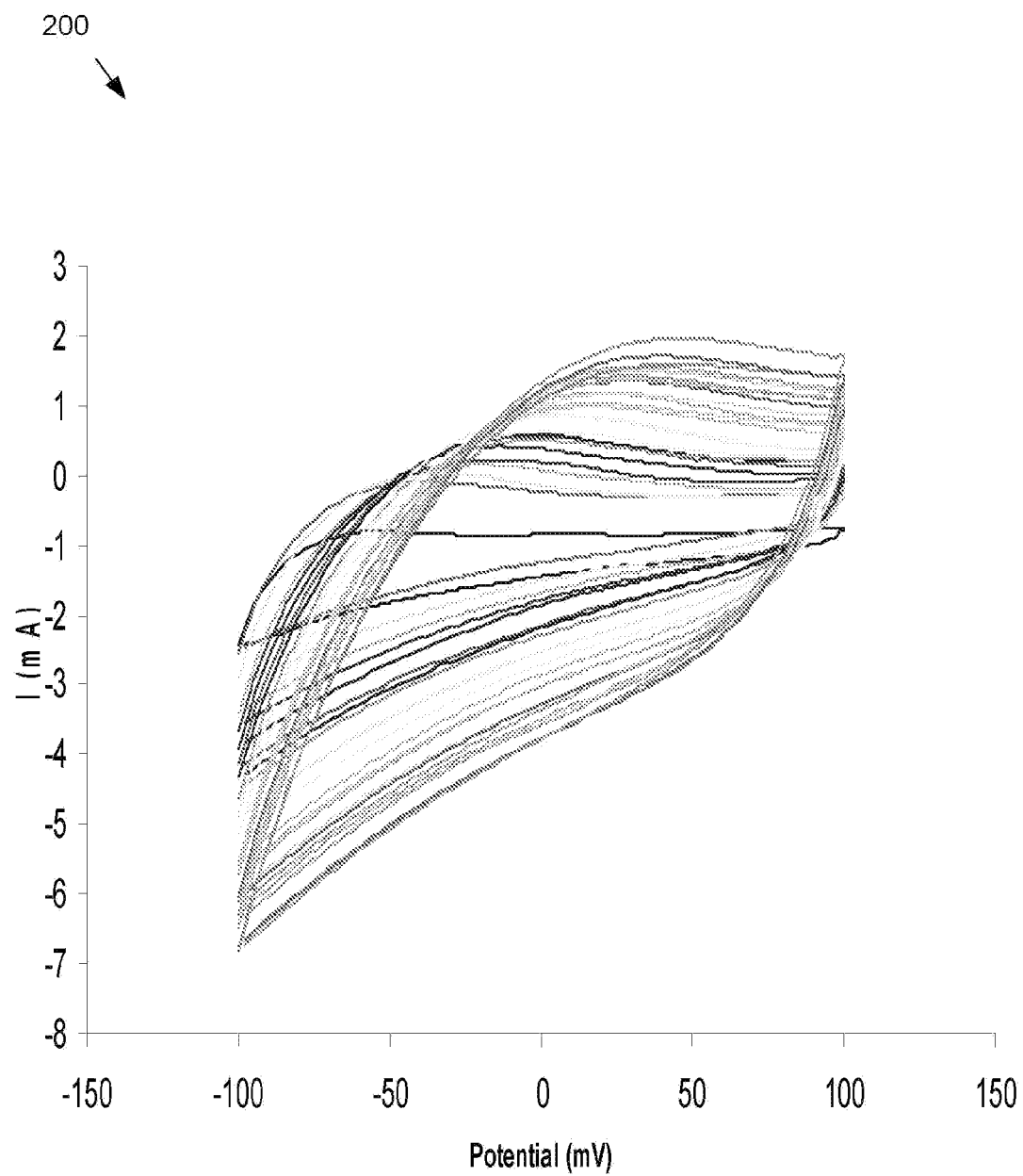
FIG. 2 depicts a set of cyclic voltammograms achieved during electrodepostion of Pt—Ir films, in accordance with exemplary embodiments of the present disclosure.

Thin film deposition cycles recorded at regular time intervals for 32 minutes were plotted in FIG. 2 to show cathodic and anodic current evolution over the deposition period. A plot 200 of the cathodic current magnitude at the most negative potential (U=−0.1V vs. Ag/AgCl) showed a steadily increasing current magnitude for most of the deposition process, suggesting a steady increase in thin films surface area. SEM micrographs of electrodeposited thin films were consistent with this observation, FIG. 5, showing a progressive increase in surface roughness with elapsed time. The growth of the Pt—Ir layers was accompanied by an overall enlargement of the active area.

Figure 3A:
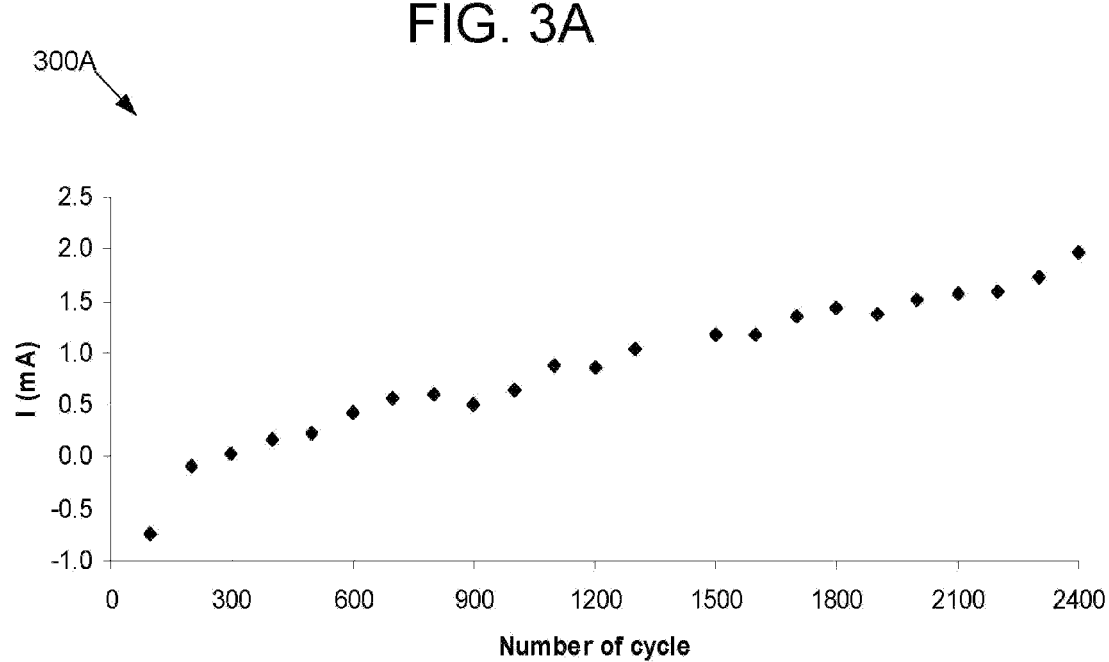
FIG. 3 depicts two plots of maximum currents as a function of number of cycles, for anodic currents (a) and cathodic currents (b), in accordance with exemplary embodiments of the present disclosure.
Figure 3B:
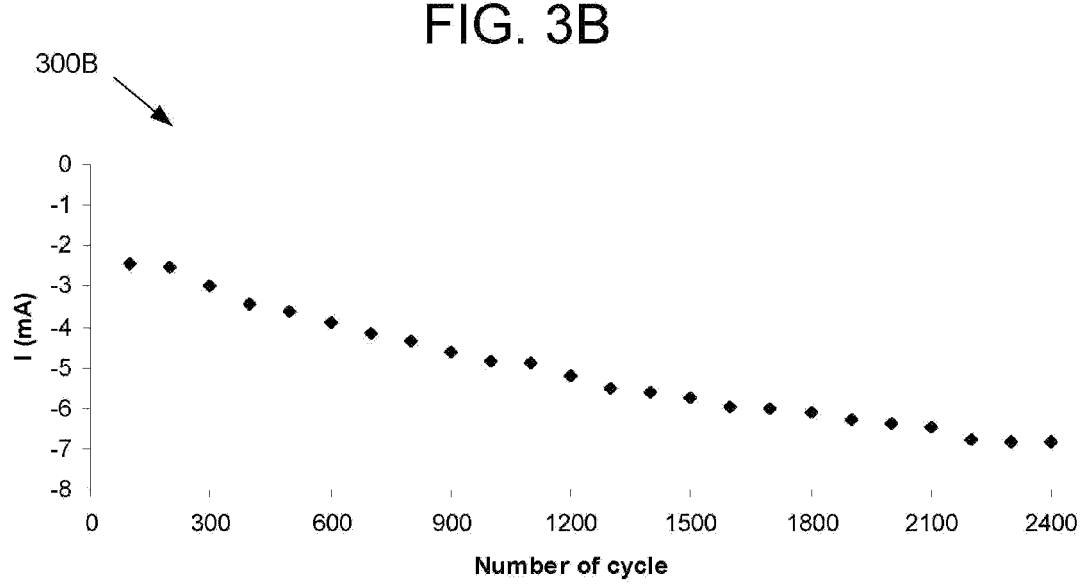

FIG. 3 includes FIG. 3A, which shows a plot 300A of the maximum anodic currents, and FIG. 3B, which shows a plot 300B of maximum cathodic currents as a function of number of cycles. In FIGS. 3A-3B, increases of the current in anodic and cathodic directions showed a linear behavior with increasing the number of cycles or deposition time. The cathodic currents are larger than the anodic currents indicating the reduction of Pt—Ir films with increased active areas.

Figure 4A:
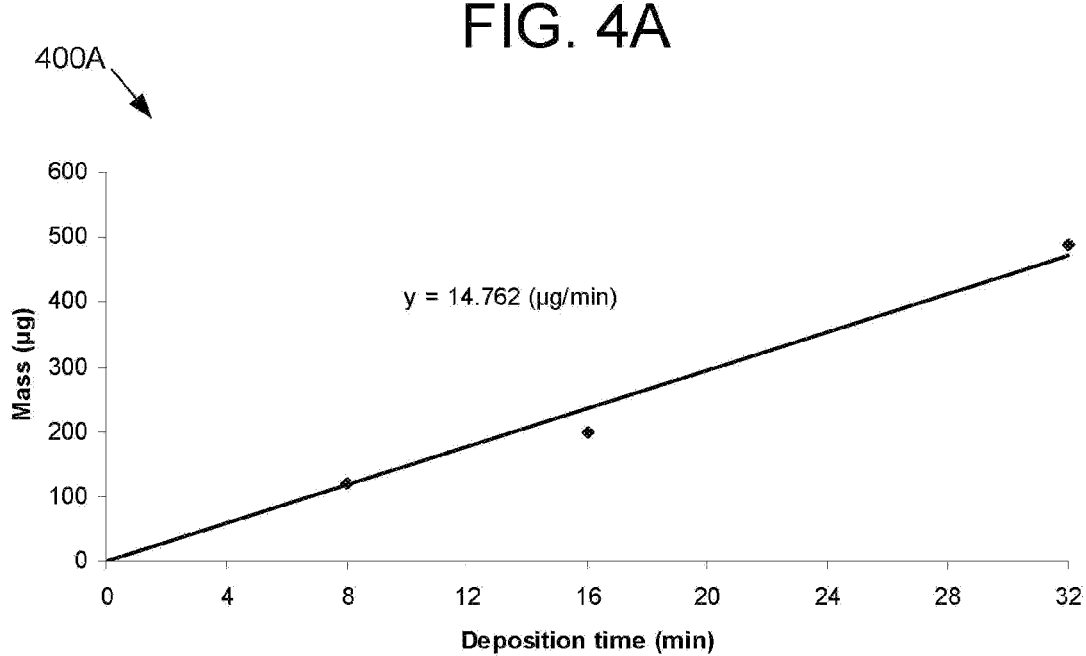
FIG. 4. depicts two plots of coating properties vs. deposition time, mass vs. deposition time (a) and coating thickness vs. deposition time (b), in accordance with exemplary embodiments of the present disclosure.
Figure 4B:
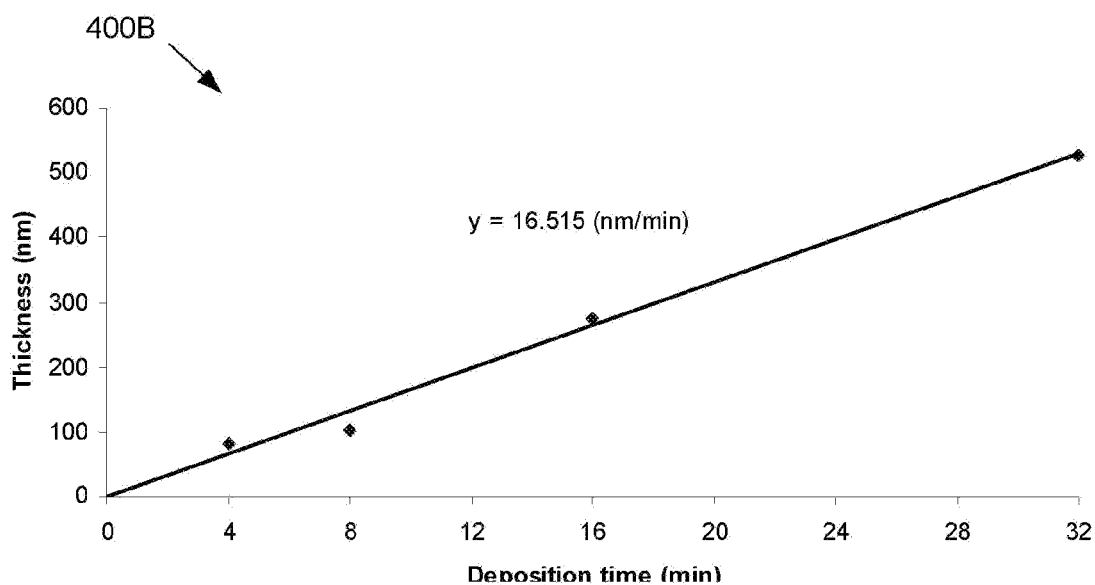

Pt—Ir deposition rate was characterized via mass change measurement and profilometry measurement. Profilometry scans were taken over the central 5 mm of the electrodeposited Pt—Ir films. FIG. 4, includes FIGS. 4A-4B, which depict two plots of coating properties vs. deposition time, mass vs. deposition time 400A and coating thickness vs. deposition time 400B, in accordance with exemplary embodiments of the present disclosure. Based on both profilometry and deposited mass data, Pt—Ir films showed relatively constant growth rate over the elapsed time period. In these figures, mass and thicknesses of the Pt—Ir electroplated films have linear relationship with deposition time and the deposition rates have measured to be 14.76 µg/min and 16.5 nm/min, respectively.

Figure 5A:
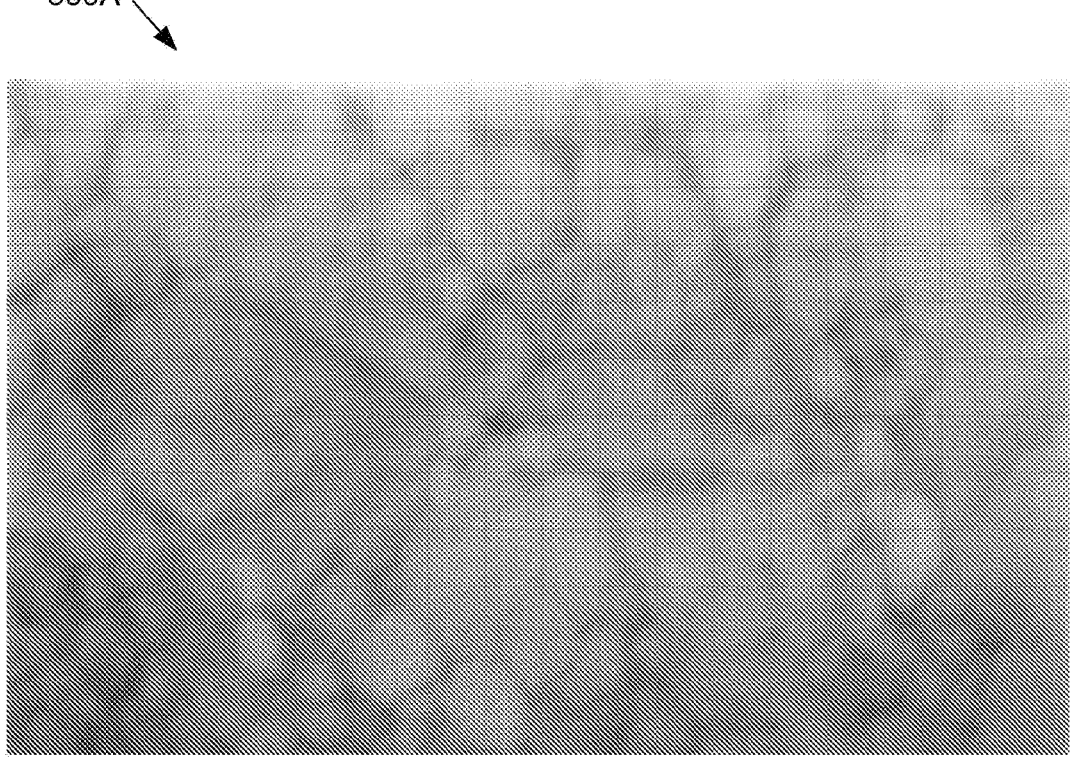
FIG. 5 depicts a set of SEM micrographs, in accordance with exemplary embodiments of the present disclosure; an Au substrate is shown in (a) and Pt—Ir films are shown in (b)-(e) with 4, 8, 16 and 32 minutes of deposition times, respectively.
Figure 5B:
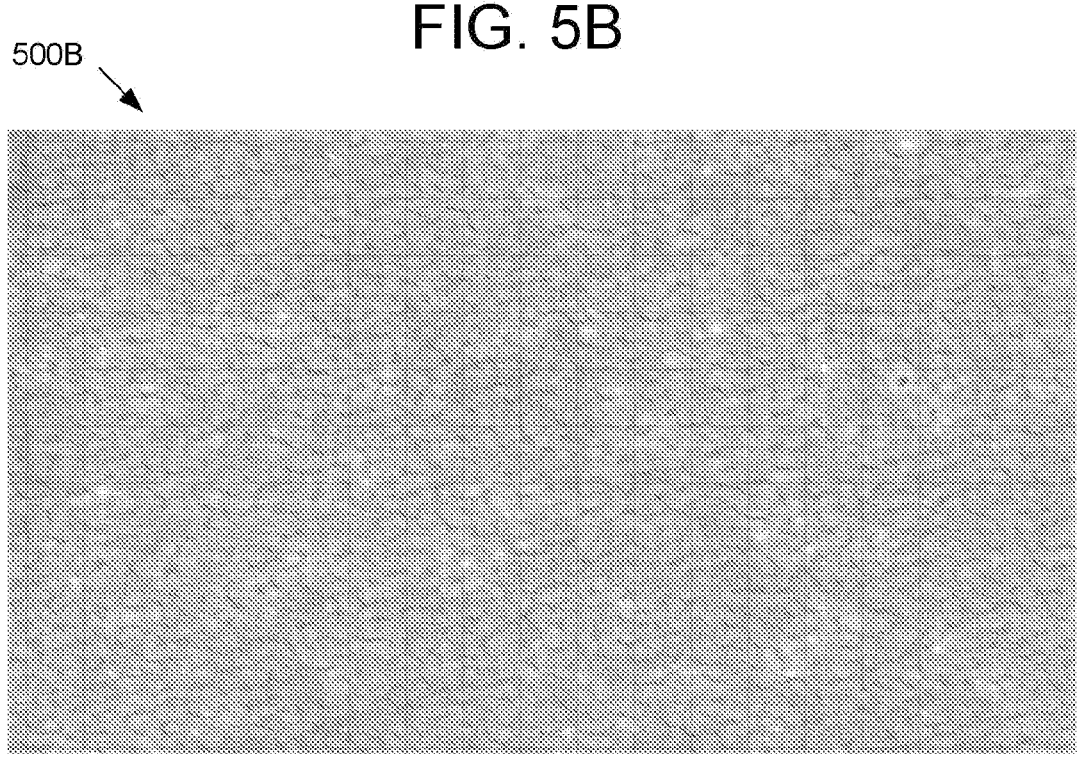
Figure 5C:
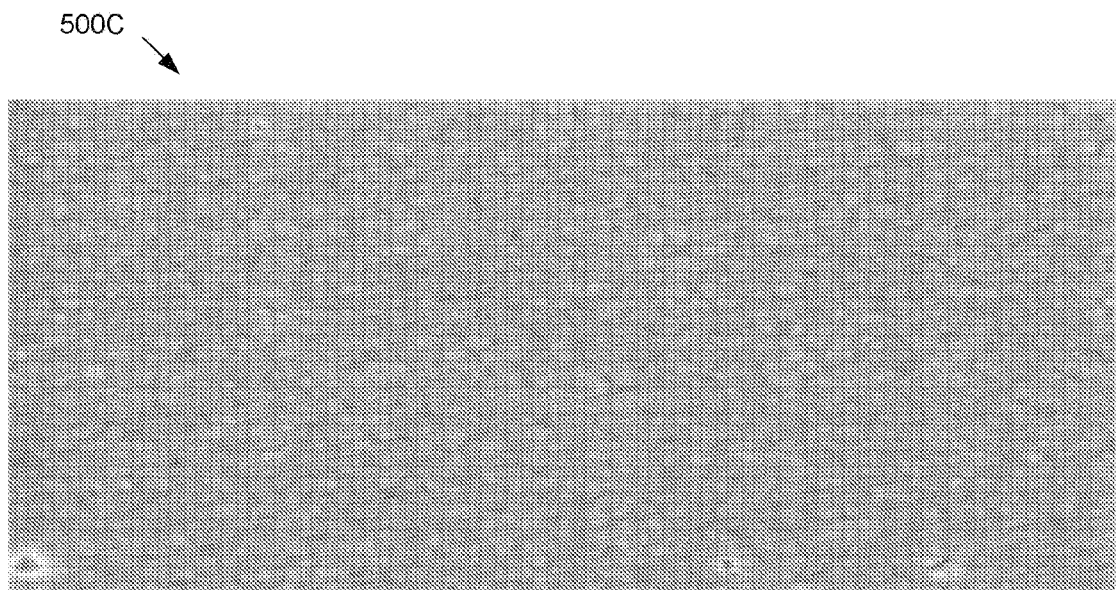
Figure 5D:
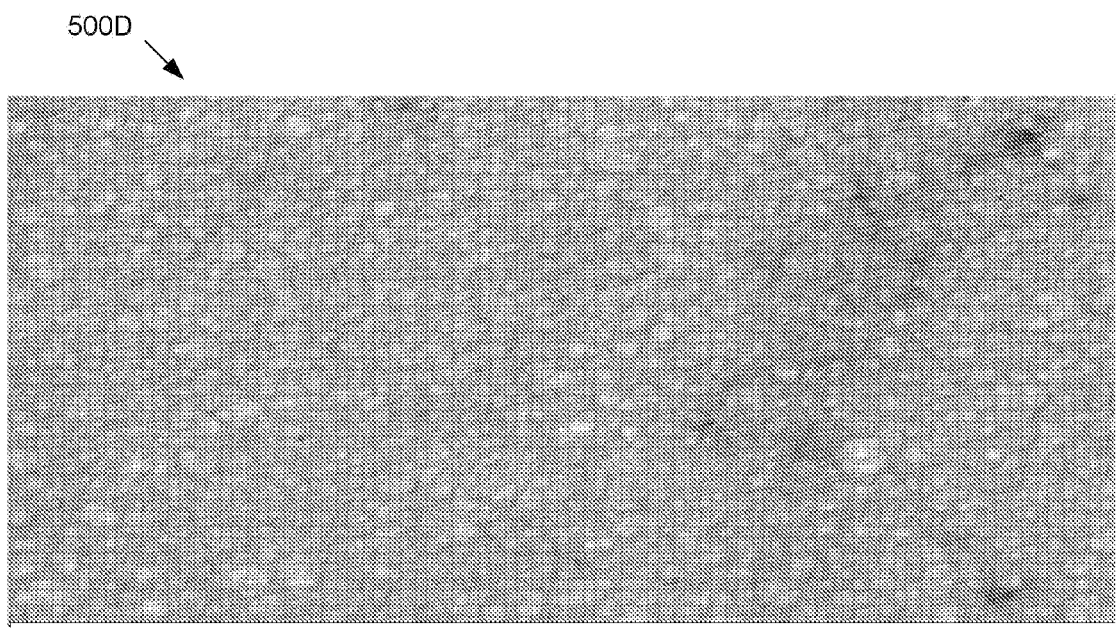
Figure 5E:
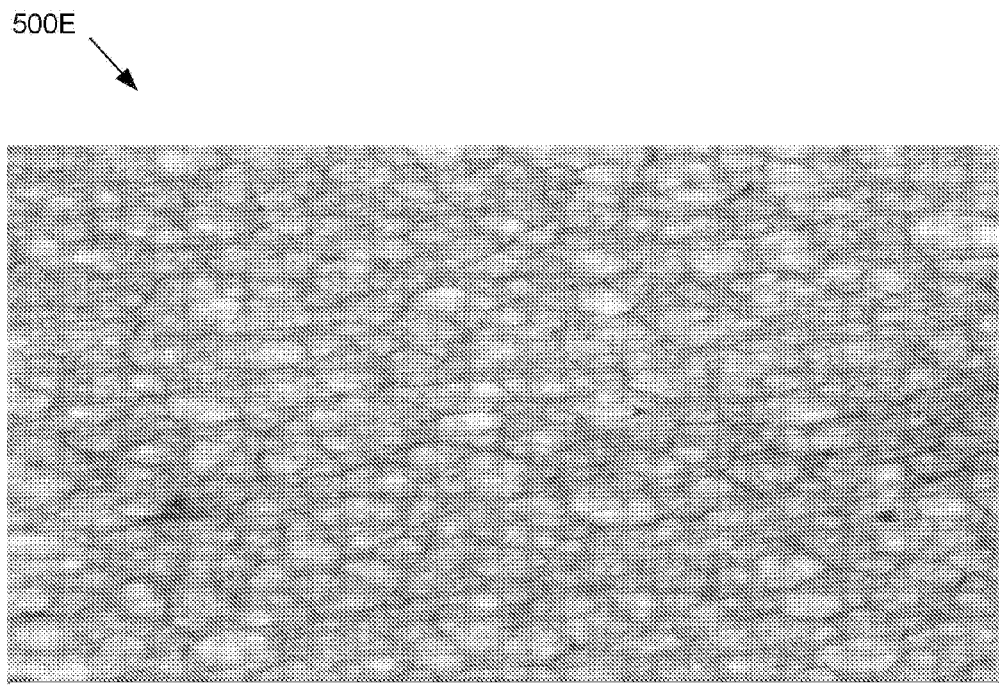

SEM micrographs of the Au substrate and the electrodeposited Pt—Ir films where taken to characterize surface morphology evolution. FIG. 5, which includes FIGS. 5A-5E, depicts a set of SEM micrographs 500A-500E, in accordance with exemplary embodiments of the present disclosure. An Au substrate is shown in FIG. 5A and Pt—Ir films are shown in FIGS. 5B-5E with four (4), eight (8), 16 and 32 minutes of deposition times, respectively; FIG. 5A shows large the grain sizes of the evaporated Au film on top of the glass slide. FIG. 5B corresponds to the Pt—Ir film grown for 4 min and presents a more uniform Pt—Ir grain size coating the surface, in comparison with the grains of the Au substrate in FIG. 5B. FIGS. 5C-5E correspond to eight (8), 16 and 32 minutes of deposition of Pt—Ir films formed on the gold substrate. Visual analysis of the micrographs suggest that the surfaces of the Pt—Ir films increase in nodular structure and morphology with increasing deposition time, FIGS. 5B-5E. The micrograph for the film obtained by four (4) minutes of deposition shows a nanocrystalline structure with size of about 25 nm. In comparison, the thin film deposited for 32 minutes shows average growth in the nanocrystals size has reached the size of 100 nm and the surfaces of the films have rougher appearance.

Quantitative compositional analysis of 80-20% Pt—Ir foil and electroplated Pt—Ir films was obtained using an electron microprobe. The samples were analyzed by wavelength dispersive spectroscopy (WDS-analysis). Accordingly, the intensities of characteristic X-ray lines produced during electron bombardment of a specimen are compared to that produced from a standard samples using similar instrumental conditions (accelerating voltage, beam current).

Table I below summarizes the chemical compositions of the 80-20% Pt—Ir control sample and electroplated Pt—Ir films, in accordance with exemplary embodiments of the present disclosure. The data in Table I show a chemical composition of about 60-40% for 4 minutes and a constant ratio of 56-44% for Pt—Ir elements; such data would seem to indicate that the deposition time after eight (8) minutes, has minimal or almost no effect on the amounts of platinum and iridium in the films.

TABLE 1

| Sample | Pt (a %) | Ir (a %) |
|---|---|---|
| Pt—Ir (80-20%) | 80.3 | 19.7 |
| 4 minutes | 60.7 | 39.3 |
| 8 minutes | 56.2 | 43.8 |
| 16 minutes | 56.5 | 43.5 |
| 32 minutes | 57.4 | 42.6 |

FIG. 6 includes FIGS. 6A-6D with plots 600A-600D, which compare cyclic voltammagrams for the Au substrate, Pt foil, Ir foil and 80-20 Pt/Ir foils in nitrogen-purged 0.05 M $H_2SO_4$ (aq) solution. The gold substrate voltammagram showed characteristic features, namely in the anodic sweep, an oxide shoulder and peak spanning from U=0.8V to U=1.2V vs. Ag/AgCl. In the cathodic sweep, the gold oxide reduction peak maximum was located at U=0.9V vs. Ag/AgCl and no other features were observed except the hydrogen reduction current beginning near −0.1V vs. Ag/AgCl. In this case, the electrode was cycled within a limited potential range and for less than 20 cycles to characterize the metal-solution interaction, therefore iridium activation was limited.

Figure 6A:
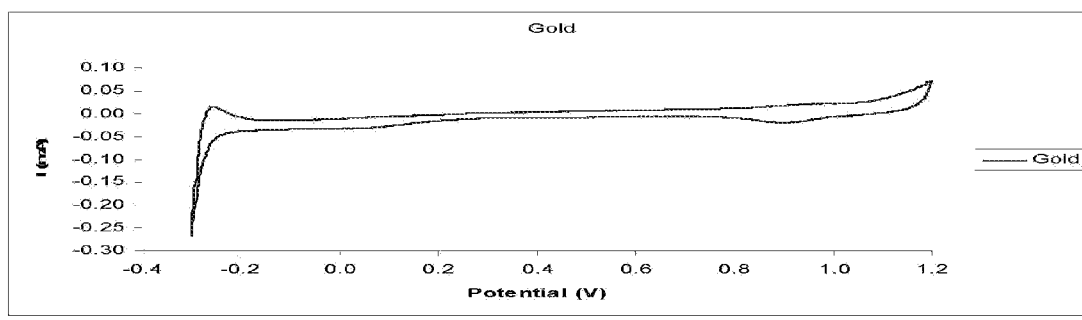
FIG. 6 depicts a set of cyclic voltammograms of an Au substrate, control samples and Pt—Ir films with different deposition times measured in 0.05 M $H_2SO_4$, in accordance with exemplary embodiments of the present disclosure.
Figure 6B:
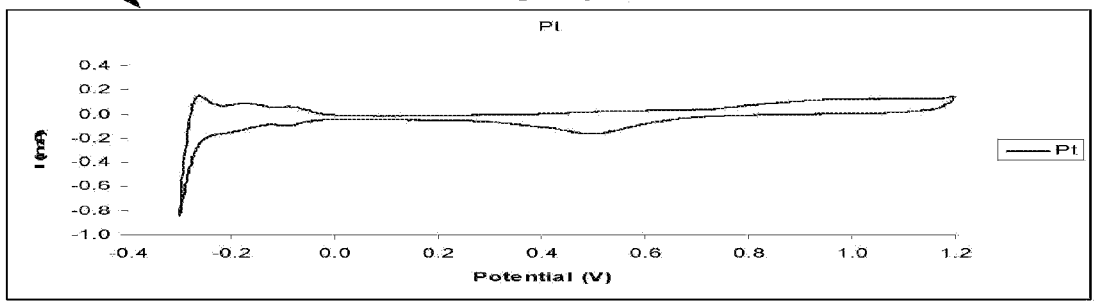
Figure 6C:
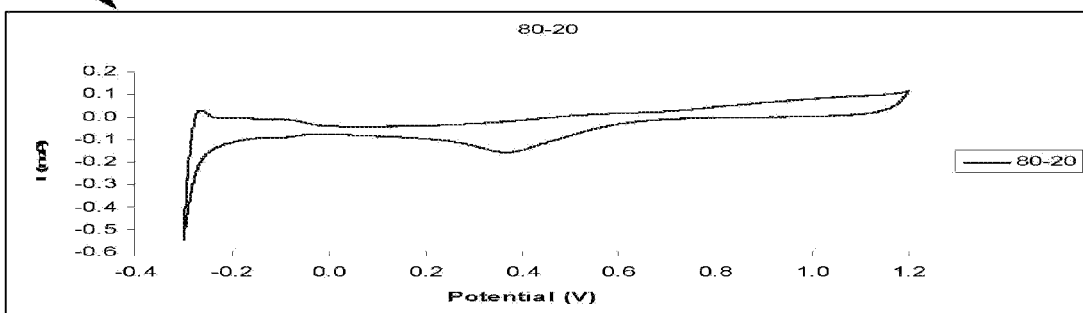
Figure 6D:
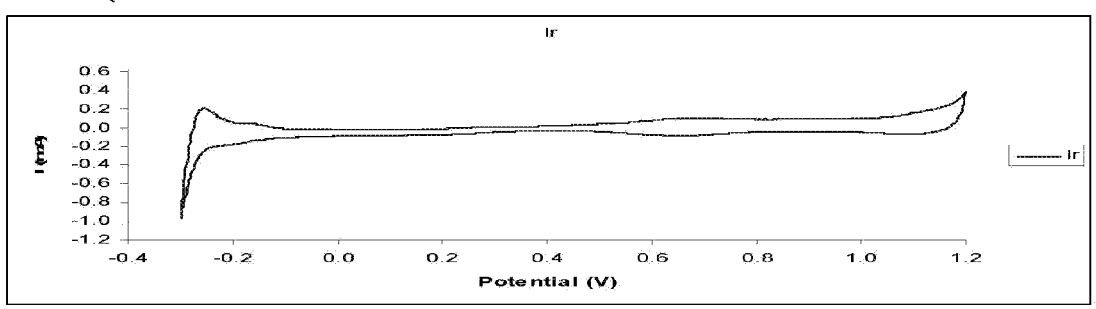
Figure 7A:
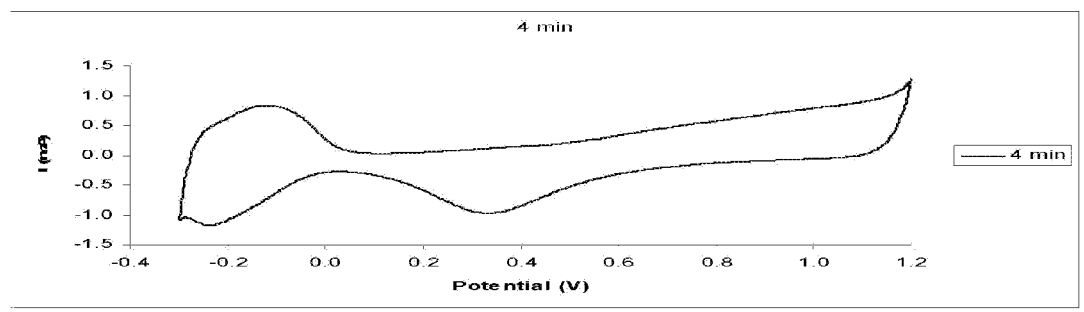
FIG. 7 depicts a set of Bode plots for Au substrate, Pt, Ir, 80-20 Pt—Ir foils, and Pt—Ir films in measured in 0.05 M $H_2SO_4$, in accordance with exemplary embodiments of the present disclosure.
Figure 7B:
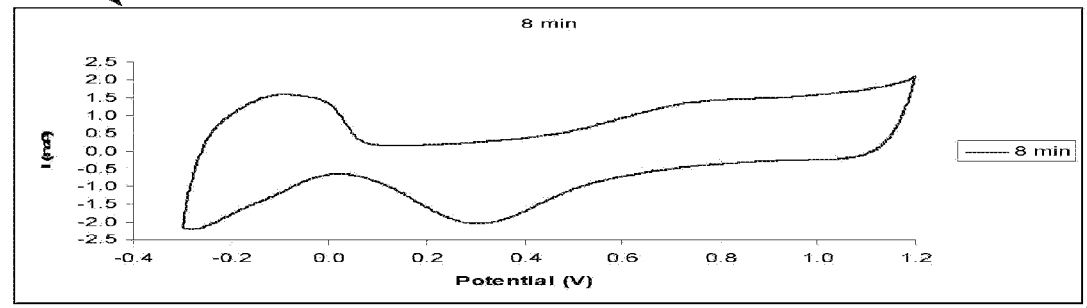
Figure 7C:
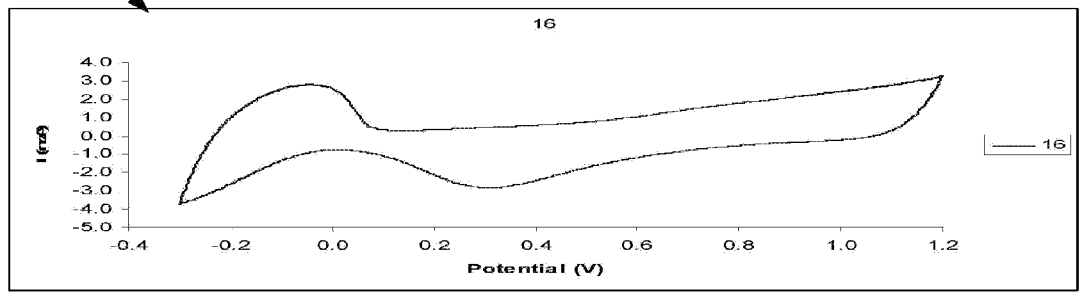
Figure 7D:
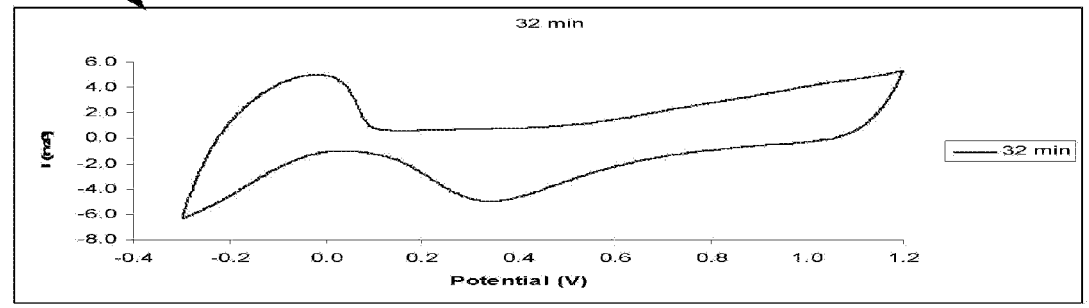

Lastly, the 80-20 Pt/Ir foil voltammagram, FIG. 6D, demonstrated a profile similar to that of the pure platinum foil, except with less pronounced hydrogen adsorption and desorption peaks, as would be expected due to the disruption in the H—Pt lattice binding sites, caused by remnant iridium oxide left on the reduced surface. The consistency of the results of these experiments with the literature suggests that the electrochemical system used was appropriate for characterizing the electrodeposited films.

FIG. 7 includes FIGS. 7A-7D, which show four plots 700A-700D that compare voltammagrams taken from the same four substrates discussed previously and compares them with voltammagrams taken from the electrodeposited thin films. For these measurements, scans ranges were extended to U=−0.3V to 1.2V vs. Ag/AgCl to capture the entire hydrogen adsorption and desorption peaks for the electrodeposited films.

For pure Pt around −0.12 and −0.22 V, hydrogen underpotential deposition, around −0.17 and 0.08 V, hydrogen oxidation and around 0.48 V, Pt reduction occurs (FIG. 6b). For Pt—Ir film with a deposition time of 4 minutes (FIG. 6e) the Pt—Ir reduction peak is shifted to around 0.35 V and for Pt—Ir films with a deposition times of 8 to 32 minutes (FIG. 6f-h), the Pt—Ir reduction peak is shifted to around 0.32 V. It was found that all electroplated Pt—Ir films (FIG. 6e-h) did not show the hydrogen adsorption/desorption peaks which can be attributed to the changes on the surface structure of Pt due to the formation of $IrO_2$ in the oxidation potential range. The number of active sites on the surface of Pt can be determined from the hydrogen adsorption and desorption and can be evaluated from the integrated intensity of these peaks which suggests that the active surface area of Pt electrodes can be determined from the adsorption/desorption of hydrogen of Pt electrodes These results suggest that, at these scan rates, the total charge capacitance of the electrodeposited electrodes is significantly greater than those of flat surface area platinum and iridium electrodes.

The Pt/Ir film has a desired composition ratio of Pt to Ir. In exemplary embodiments, the microelectrode can be cylindrical with a desired length and a diameter of between about 0.5 micron to about 200 micron (or any diameter within the range, inclusive of the end values).

Electrochemical impedance spectroscopy (EIS) data were obtained in 0.05 M $H_2SO_4$ at the open circuit potential (OCP) to assess frequency dependence of charge transfer at the electrode surface. Table 2 shows EIS data obtained.

TABLE 2

|  | Au | Pt | Pt—Ir (80-20%) | Ir | 4 min | 8 min | 16 min | 32 min |
|---|---|---|---|---|---|---|---|---|
| C (F) | $4.57*10^{-5}$ | $9.55*10^{-5}$ | $6.3*10^{-5}$ | $3.573*10^{-4}$ | $1.55*10^{-3}$ | $5.21*10^{-3}$ | $1.11*10^{-2}$ | $2.01*10^{-2}$ |
| $R_p$ (kohm) | 650 | 815 | 820 | 241 | 78 | 17 | 7.8 | 4.3 |
| $R_s$ (ohm) | 21.67 | 22.08 | 22.49 | 23.06 | 21.03 | 21.13 | 21.28 | 21.09 |
| τ (s) | 29.7 | 77.8 | 51.7 | 86.3 | 120.9 | 88.4 | 85.8 | 86.43 |

The Bode plots in FIG. 7 for all samples and the impedance of the electroplated Pt—Ir films were observed to drastically decrease by increasing the deposition time due to increased surface area. The impedances for all films compared with the uncoated Au substrate was observe to be reduced by more than a factor of 10.

Figure 8:
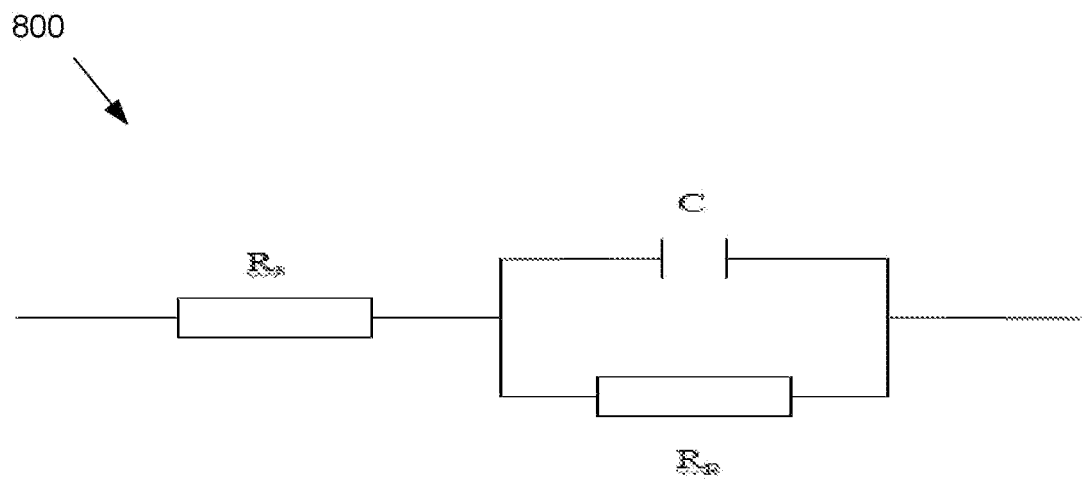
FIG. 8 depicts an equivalent circuit to the electrochemical cell of FIG. 1.

FIG. 8 depicts an equivalent circuit 800 to the electrochemical cell of FIG. 1. The EIS results of electroplated Pt—Ir films that were tested follow the one-time constant model with the equivalent circuit shown in FIG. 8, in which the solution resistance $R_s$ is in series with a parallel combination of the capacitance of the electrode C and polarization resistance $R_p$.

Figure 9:
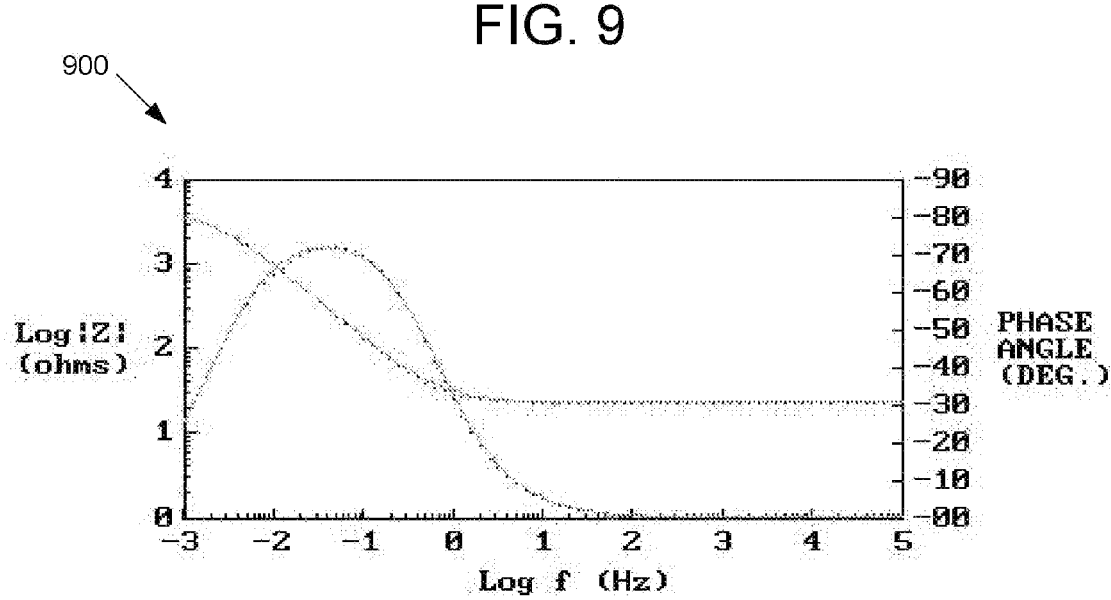
FIG. 9 depicts Bode plots of experimental (dots) and fit data (solid line) of Pt—Ir film electroplated for 32 minutes, in accordance with exemplary embodiments of the present disclosure.
Figure 9A:
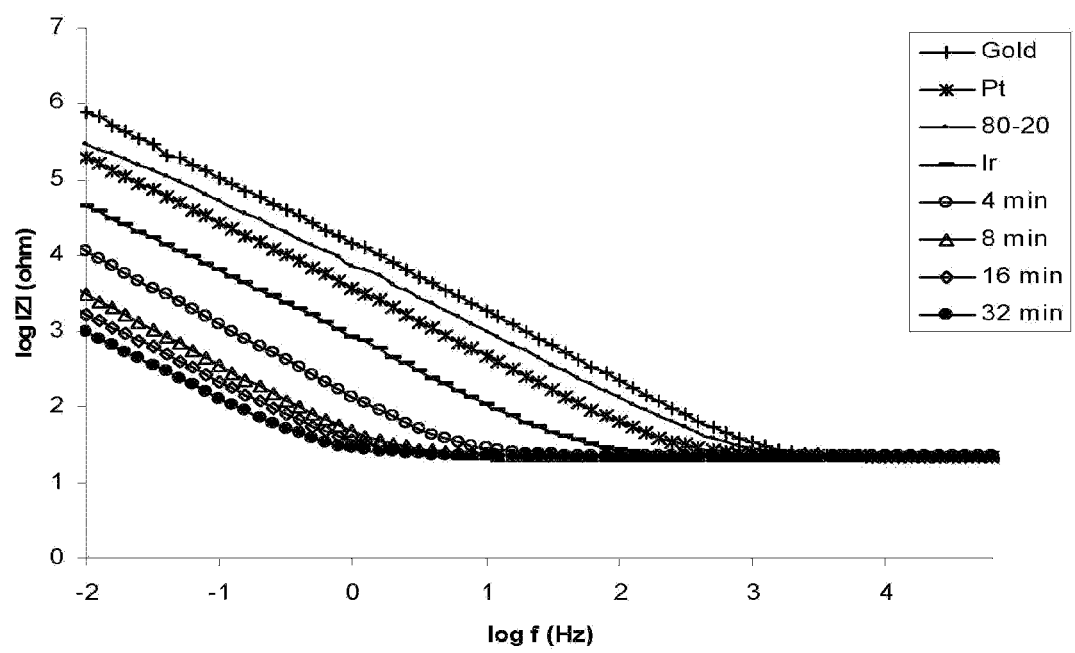
Figure 9B:
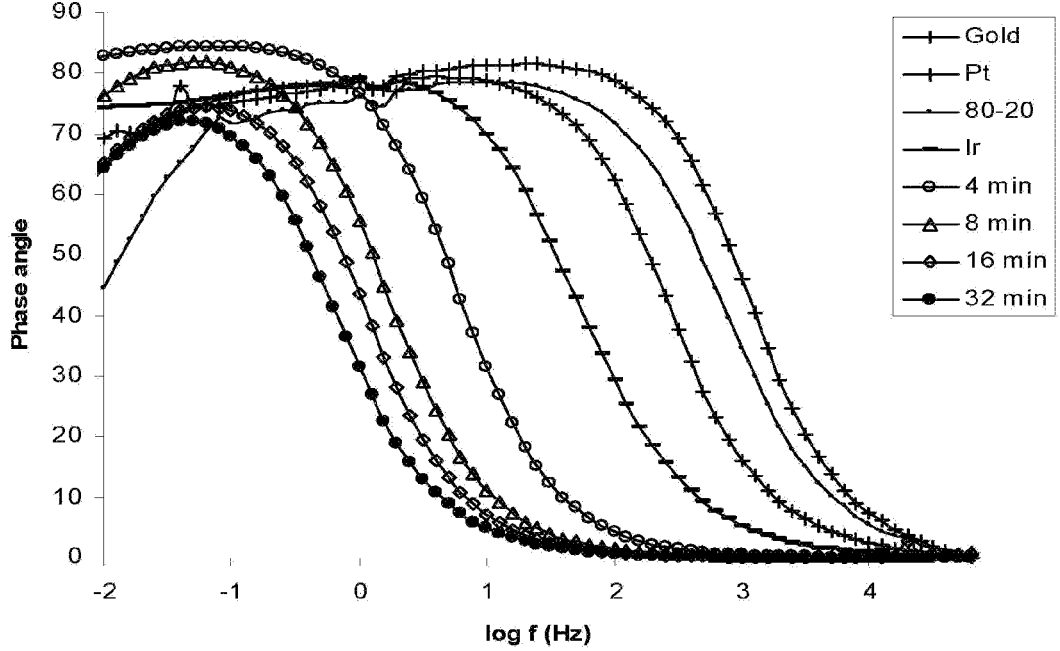

FIG. 9, includes FIGS. 9A and 9B, which show two Bode plots 900(A)-900(B) of experimental and fit data of a Pt—Ir film electroplated for 32 minutes, in accordance with a tested embodiment of the present disclosure. The plots 900(A)-900(B) seem to indicate that the fit data are in excellent agreement with the experimental data.

The time constant τ=C*Rp values in Table 2 show similar values for all electroplated Pt—Ir films indicating that by increasing the C for longer deposition times, the $R_p$ has decreased which proves that the increased surface area is the only effective factor on the changes of the C values.

Figure 10A:
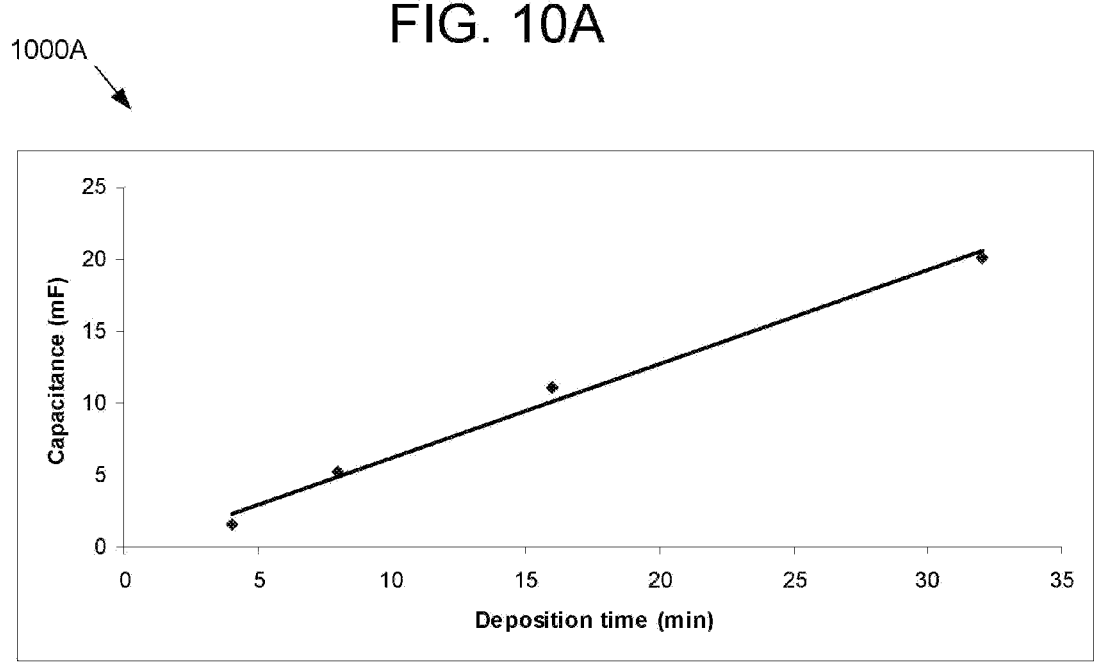
FIG. 10 depicts capacitance (a) and 1/Rp (b) values vs. deposition time for electrodeposited Pt—Ir films, in accordance with exemplary embodiments of the present disclosure.
Figure 10B:
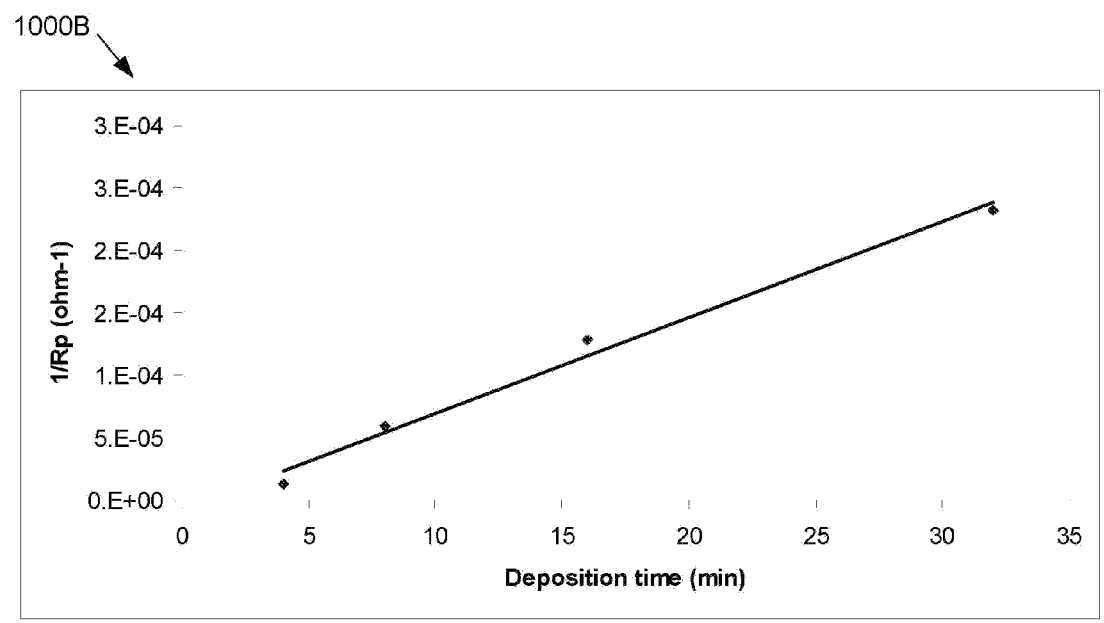

FIG. 10, including FIGS. 10A-10B, depict plots 1000A-1000B indicating a linear relationship between the C, in (a), and $1/R_p$, in (b), and the deposition time. The plots 1000A-1000B would appear to indicate that the increase in the Pt—Ir films thickness occurs in constant rate and is generally independent of deposition time.

Figure 11:
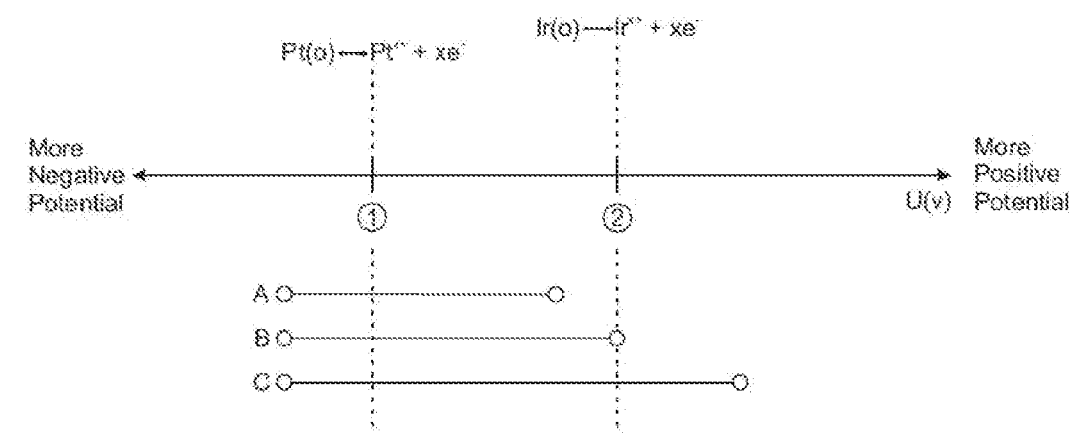
FIG. 11 depicts an electrochemical potential scale showing equilibrium potentials for Pt salts and Ir salts, in accordance with exemplary embodiments of the present disclosure.

FIG. 11 depicts a diagram 1100 of an electrochemical potential scale showing equilibrium potentials for Pt salts and Ir salts, in accordance with exemplary embodiments of the present disclosure. The scale of electrochemical potentials shows an arbitrary equilibrium potential for a Pt salt (1) and a Ir salt (2). The potential range for deposition can, according to embodiments of the present disclosure, span any of the following ranges: (A) the range may have a negative limit below (1) and a positive limit below (2); the range may have a negative limit below (1) and a positive limit equal to (2); and, the range may have a negative limit below (1) and a positive limit more positive than (2).

The following are details of an exemplary Pt—Ir film deposition protocol:

For an exemplary tested embodiment, a Pt—Ir electrodeposition bath was prepared using 0.2 gr/l of Sodium hexachloroiridate (III) hydrate, Ir 31.5% min ($Na_3IrCl_6 \cdot xH_2O$) and 0.186 gr/l Sodium hexachloroplatinate (IV) hexahydrate ($Na_2PtCl_6 \cdot 6H_2O$) in gr/l of 0.1 M nitric acid ($HNO_3$). For electrodepostion of smooth Pt—Ir thin films, an ultrasonic homogenizer was used, producing 20 kHz at amplitude of 20 (5 W); where an amplitude of 20 means 20% of total instrument output for the sonicator. The sonicator was a Misonix s-4000 Ultrasonic Processor. The electrodeposition bath temperature used started around 56 C and the finishing bath temperature was 62 C. An electrodeposition time of 32 minutes was observed to form about 0.45 μm of smooth 60-40% Pt—Ir thin film. For the deposition technique, cyclic voltammetry was employed utilizing a scan rate: 500 mV/s.

For the Electrodepostion of rough Pt—Ir thin films, a chemical was added to the prepared Pt—Ir electrodeposition bath, i.e., 40 g/l of $K_2SO_4$. Am ultrasonic homogenizer was used, with 20 kHz at amplitude of 37 (8 W). The electrodeposition bath temperature started around 56 C and finished at 75 C. The electrodeposition time was 17 minutes, which was observed to form 0.8 μm of rough 60-40% Pt—Ir film. For the deposition, the applied potential technique was a potential sweep, with a scan rate 0.2 mV/s.

Accordingly, as described above, aspects and embodiments of the present disclosure can provide advantages and benefits compared with previous techniques.

The components, steps, features, benefits and advantages that have been discussed are merely illustrative. None of them, nor the discussions relating to them, are intended to limit the scope of protection in any way. Numerous other embodiments are also contemplated. These include embodiments that have fewer, additional, and/or different components, steps, features, objects, benefits and advantages. These also include embodiments in which the components and/or steps are arranged and/or ordered differently.

In reading the present disclosure, one skilled in the art will appreciate that embodiments of the present disclosure can be implemented in hardware, software, firmware, or any combinations of such, and over one or more networks. Suitable software can include computer-readable or machine-readable instructions for performing methods and techniques (and portions thereof) of designing and/or controlling the implementation of tailored RF pulse trains. Any suitable software language (machine-dependent or machine-independent) may be utilized. Moreover, embodiments of the present disclosure can be included in or carried by various signals, e.g., as transmitted over a wireless RF or IR communications link or downloaded from the Internet.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

All articles, patents, patent applications, and other publications which have been cited in this disclosure are hereby incorporated herein by reference.

The phrase "means for" when used in a claim is intended to and should be interpreted to embrace the corresponding structures and materials that have been described and their equivalents. Similarly, the phrase "step for" when used in a claim embraces the corresponding acts that have been described and their equivalents. The absence of these phrases means that the claim is not intended to and should not be interpreted to be limited to any of the corresponding structures, materials, or acts or to their equivalents.

Nothing that has been stated or illustrated is intended or should be interpreted to cause a dedication of any component, step, feature, benefit, advantage, or equivalent to the public, regardless of whether it is recited in the claims.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents.

What is claimed is:

1. A method of depositing a platinum-iridium thin film on a base, the method comprising:
    preparing an electrolyte solution by heating an aqueous solution to boiling, then cooling the aqueous solution to room temperature under a non-oxidizing atmosphere, wherein the aqueous solution contains metal that consists essentially of platinum and iridium or of salts containing platinum and iridium;
    causing contact between a metal base and the electrolyte solution for electrodeposition, wherein the electrolyte solution is non-cytotoxic;
    causing contact between two or more electrodes and the electrolyte solution, wherein the electrodes are configured to apply an electric potential to the electrolyte solution;
    by use of the electrolyte solution, causing electrical contact between at least one of the two or more electrodes and the metal base;
    applying the electric potential to the two or more electrodes in the electrolyte solution in an amount sufficient to cause deposition of Pt and Ir on the metal base, wherein applying the electric potential comprises sweeping the electric potential over a range of voltages; and
    forming a deposited thin film on the base, wherein the thin film has a desired composition of Pt and Ir,
    wherein, during the step of applying the electric potential to the electrodes, the electrolyte solution is agitated with an ultrasonic homogenizer.

2. The method of claim 1, further comprising heating the electrolyte solution to improve stability of the electrolyte solution.

3. The method of claim 1, wherein the electrolyte solution is lead free.

4. The method of claim 1, wherein the prepared electrolyte solution has a near neutral pH between about 6 to about 8.

5. The method of claim 1, wherein the electrolyte solution has a pH from about 1.5 to 2.5.

6. The method of claim 1, wherein applying the electric potential produces the deposited thin film having a desired electrochemical impedance.

7. The method of claim 1, wherein applying the electric potential produces the deposited thin film having a desired surface roughness.

8. The method of claim 1, wherein applying the electric potential produces the deposited thin film having a desired porosity or lack thereof.

9. The method of claim 1, wherein the composition of the thin film is about 80% Pt and 20% Ir.

10. The method of claim 1, wherein the composition of the thin film is about 60% Pt and 40% Ir.

11. The method of claim 1, wherein the composition of the thin film is about 95% Pt and 5% Ir.

12. The method of claim 1, wherein the prepared electrolyte solution comprises sodium hexachloroiridate (III) hydrate ($Na_3IrCl_6 \cdot xH_2O$) and sodium hexachloroplatinate (IV) hexahydrate ($Na_2PtCl_6 \cdot 6H_2O$).

13. The method of claim 12, wherein the aqueous solution further contains nitric acid ($HNO_3$).

14. The method of claim 12, wherein the preparing the electrolyte solution further comprises adding a salt to the aqueous solution that increases surface roughness.

15. The method of claim 14, wherein the salt comprises potassium sulfate ($K_2SO_4$).

16. The method of claim 1, wherein the composition of the thin film is in the range from about 98% Pt and 2% Ir to about 60% Pt and about 40% Ir.

17. The method of claim 1, wherein the composition of the thin film is in the range from about 90% Pt and 10% Ir to about 60% Pt and about 40% Ir.

18. The method of claim 1, wherein the composition of the thin film is in the range from about 98% Pt and 2% Ir to about 90% Pt and about 10% Ir.

19. The method of claim 1, further comprising controlling a deposition time to achieve a desired ratio of Pt to Ir of the deposited thin film.

20. The method of claim 1, further comprising controlling a deposition time to achieve a desired a surface roughness of the thin film.

21. The method of claim 1, further comprising controlling a deposition time to achieve a desired resistance of the thin film.

22. A method of depositing a platinum-iridium thin film on a base, the method comprising:
preparing an electrolyte solution by heating an aqueous solution to boiling, then cooling the aqueous solution to room temperature under a non-oxidizing atmosphere, wherein the aqueous solution contains metal that consists essentially of platinum and iridium or of salts containing platinum and iridium;
causing contact between a metal base and the electrolyte solution for electrodeposition, wherein the electrolyte solution is non-cytotoxic;
causing contact between two or more electrodes and the electrolyte solution, wherein the electrodes are configured to apply an electric potential to the electrolyte solution;
by use of the electrolyte solution, causing electrical contact between at least one of the two or more electrodes and the metal base;
applying the electric potential to the two or more electrodes in the electrolyte solution in an amount sufficient to cause deposition of Pt and Ir on the metal base; and
forming a deposited thin film on the base, wherein the thin film has Pt and Ir.

* * * * *